United States Patent
Azar et al.

(10) Patent No.: US 9,251,585 B2
(45) Date of Patent: Feb. 2, 2016

(54) COREGISTRATION AND ANALYSIS OF MULTI-MODAL IMAGES OBTAINED IN DIFFERENT GEOMETRIES

(75) Inventors: Fred S. Azar, Princeton, NJ (US); Arjun G. Yodh, Menion, PA (US); Regine Choe, Menion, PA (US); Kijoon Lee, Singapore (SG)

(73) Assignee: Siemens Aktiengesellschaft, Munich (DE)

( * ) Notice: Subject to any disclaimer, the term of this patent is extended or adjusted under 35 U.S.C. 154(b) by 1672 days.

(21) Appl. No.: 12/169,081

(22) Filed: Jul. 8, 2008

(65) Prior Publication Data

US 2009/0135191 A1 May 28, 2009

Related U.S. Application Data

(60) Provisional application No. 60/949,319, filed on Jul. 12, 2007.

(51) Int. Cl.
| | |
|---|---|
| *G09G 5/00* | (2006.01) |
| *G06T 7/00* | (2006.01) |
| *A61B 6/00* | (2006.01) |
| *G01R 33/48* | (2006.01) |
| *G01R 33/56* | (2006.01) |

(52) U.S. Cl.
CPC .............. *G06T 7/0034* (2013.01); *A61B 6/502* (2013.01); *A61B 6/5247* (2013.01); *G01R 33/4808* (2013.01); *G01R 33/5608* (2013.01); *G06T 7/0038* (2013.01); *G06T 7/0081* (2013.01); *G06T 2207/10088* (2013.01); *G06T 2207/10101* (2013.01); *G06T 2207/30068* (2013.01)

(58) Field of Classification Search
CPC ...... G06K 9/32; G06T 3/0068; G06T 3/0075; G06T 15/08
USPC .......... 382/128, 131, 133, 180, 294; 345/522; 600/407
See application file for complete search history.

(56) References Cited

U.S. PATENT DOCUMENTS

2007/0248251 A1* 10/2007 Liao et al. ............... 382/128
2008/0008401 A1* 1/2008 Zhu et al. ............... 382/294

(Continued)

OTHER PUBLICATIONS

"Coregistration of Dynamic Contrast Enhanced MRI and Broadband Diffuse Optical Spectroscopy for Characterizing Breast Cancer", David Hsiang, Natasha Shah, Hon Yu, Min-Ying Sy et al, Technology in Cancer Research & Treatment, vol. 4, No. 5, Oct. 2005.*

(Continued)

*Primary Examiner* — Aaron M Richer
*Assistant Examiner* — Weiming He

(57) ABSTRACT

A method for coregistration of multi-modal images obtained in different geometries includes acquiring multi-modal image data, wherein the multi-model image data includes image data of a first modality and image data of a second modality, wherein the image data of the respective modalities have different geometries, defining a volume of interest in the multi-modal image data, segmenting the image data of the first modality and incorporating segmentation data of the first modality into a reconstruction of the second modality, and applying a registration of the second modality image data to the first modality image data according to a similarity measure through the volume of interest, wherein an output of the registration comprises superimposed multi-modal image data.

20 Claims, 5 Drawing Sheets

(56) References Cited

U.S. PATENT DOCUMENTS

2009/0074264 A1* 3/2009 Pekar et al. .................. 382/128
2010/0067755 A1* 3/2010 Chan et al. ................... 382/128

OTHER PUBLICATIONS

Vasilis Ntziachristos, A.G. Yodh, Mitchell Schnall, and Britton Chance, "Concurrent MRI and diffuse optical tomography of breast after indocyanine green enhancement", PNAS, Mar. 14, 2000, vol. 97, No. 6, pp. 2767-2772.*

Azar, et al. A Software Platform for Visualization & Multimodal Registration of Diffuse Optical Tomography and MRI of Breast Cancer; Published by Proc. of SPIE, vol. 6081, 2006 (pp. 1-10); Magazine.

Khamene, A Novel Projection Based Approach for Medical Image Registration; et al. Published in WBIR 2006, Lecture Notes in Computer Science 4057, Springer, 2006 (pp. 247-256); Magazine.

* cited by examiner

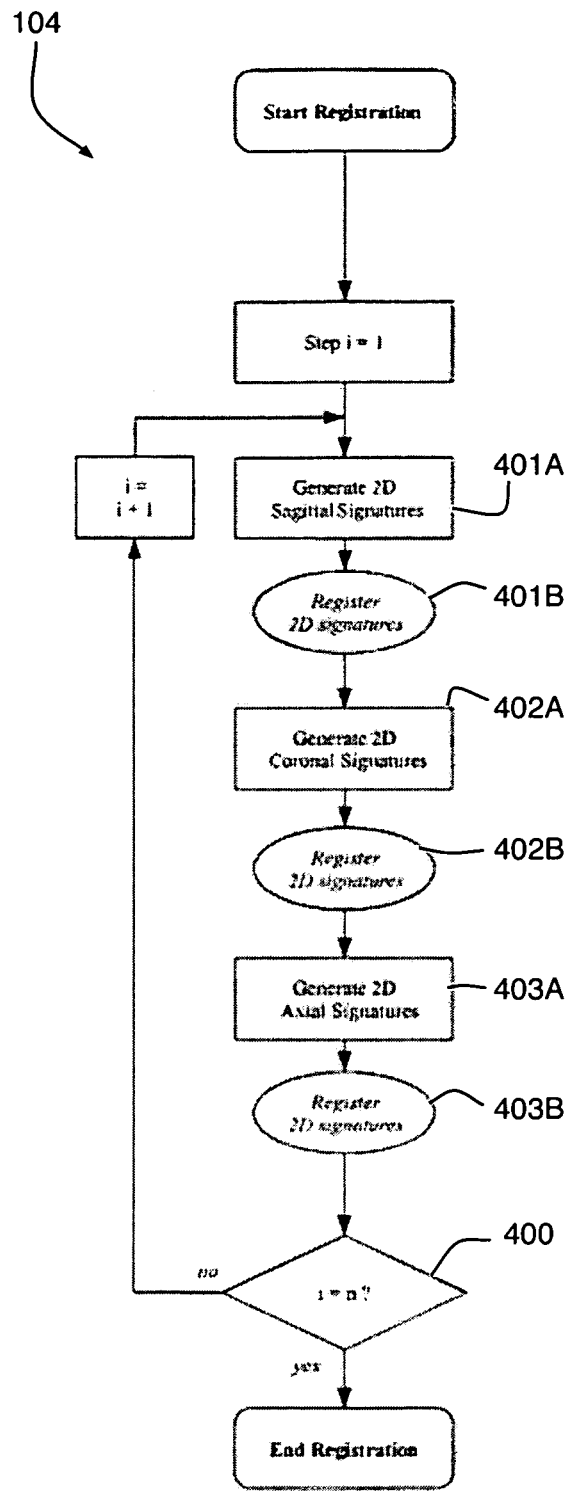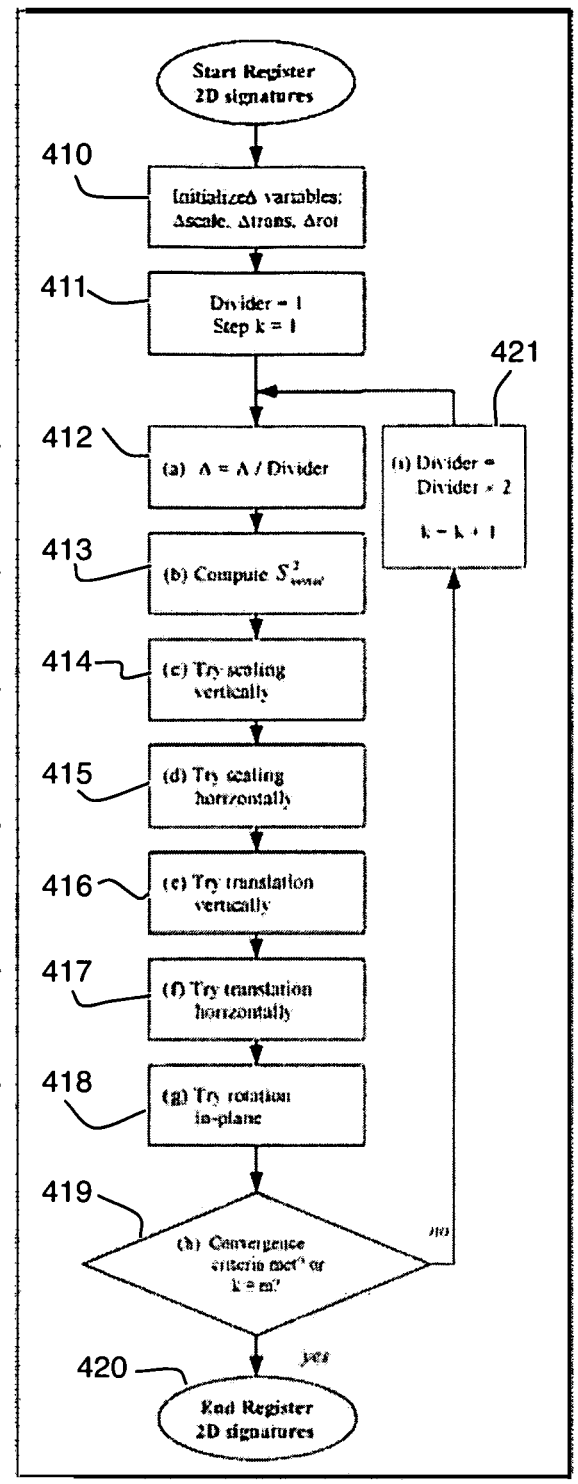
FIG. 4A
FIG. 4B

COREGISTRATION AND ANALYSIS OF MULTI-MODAL IMAGES OBTAINED IN DIFFERENT GEOMETRIES

CROSS-REFERENCE TO RELATED APPLICATIONS

This application claims the benefit of Provisional Application No. 60/949,319 filed on Jul. 12, 2007 in the United States Patent and Trademark Office, the contents of which are herein incorporated by reference in its entirety.

BACKGROUND OF THE INVENTION

1. Technical Field

The present disclosure relates to imaging, and more particularly to a system and method for multimodal imaging for research assessment and diagnosis.

2. Description of Related Art

Near-infrared (NIR) diffuse optical tomography (DOT) relies on functional processes, and provides unique measurable parameters with potential to enhance breast tumor detection sensitivity and specificity. For example, several groups have demonstrated the feasibility of breast tumor characterization based on total hemoglobin concentration, blood oxygen saturation, water and lipid concentration and scattering.

The functional information derived with DOT is complementary to structural and functional information available to conventional imaging modalities such as magnetic resonance imaging MRI, x-ray mammography, and ultrasound. Thus the combination of functional data from DOT with structural/anatomical data from other imaging modalities holds potential for enhancing tumor detection sensitivity and specificity. To achieve this goal of data fusion, two general approaches can be employed. The first, concurrent imaging, physically integrates the DOT system into the conventional imaging instrument. This approach derives images in the same geometry and at the same time. The second approach, non-concurrent imaging, employs optimized stand-alone DOT devices to produce 3-D images that must then be combined with those of the conventional imaging modalities via software techniques. In this case, the images are obtained at different times and often in different geometries.

Few DOT systems have been physically integrated into conventional imaging modalities such as MRI, 18-22 x-ray mammography, and ultrasound for concurrent measurements. By doing so, however, these DOT systems can be limited by the requirements of the "other" imaging modality, for example, restrictions on metallic instrumentation for MRI, hard breast compression for x-ray mammography, limited optode combinations for ultrasound and MRI, x-ray, and time constraints. On the other hand, among the standalone DOT systems available today, few attempts have been made to quantitatively compare DOT images of the same breast cancer patient to those of other imaging modalities obtained at different times, because the non-concurrent co-registration problem presents many challenges.

Therefore, a need exists for quantitative and systematic methods for data fusion that utilize the high-quality data and versatility of the stand-alone imaging systems.

SUMMARY OF THE INVENTION

According to an embodiment of the present disclosure, a method for coregistration of multi-modal images obtained in different geometries includes acquiring multi-modal image data, wherein the multi-model image data includes image data of a first modality and image data of a second modality, wherein the image data of the respective modalities have different geometries, defining a volume of interest in the multi-modal image data, segmenting the image data of the first modality and incorporating segmentation data of the first modality into a reconstruction of the second modality, and applying a registration of the second modality image data to the first modality image data according to a similarity measure through the volume of interest, wherein an output of the registration comprises superimposed multi-modal image data.

BRIEF DESCRIPTION OF THE DRAWINGS

Preferred embodiments of the present invention will be described below in more detail, with reference to the accompanying drawings:

FIG. 3A-D illustrate different transformation models, wherein FIG. 3A is an original image, FIG. 3B is a rigid transformation, FIG. 3C is an affine transformation, and FIG. 3D is a free-form transformation according to an embodiment of the present disclosure;

FIG. 4A is a flow chart of a global registration method according to an embodiment of the present disclosure according to an embodiment of the present disclosure;

FIG. 4B is a flow chart of a 2-D signatures registration method according to an embodiment of the present disclosure according to an embodiment of the present disclosure;

DETAILED DESCRIPTION OF PREFERRED EMBODIMENTS

Figure 1:
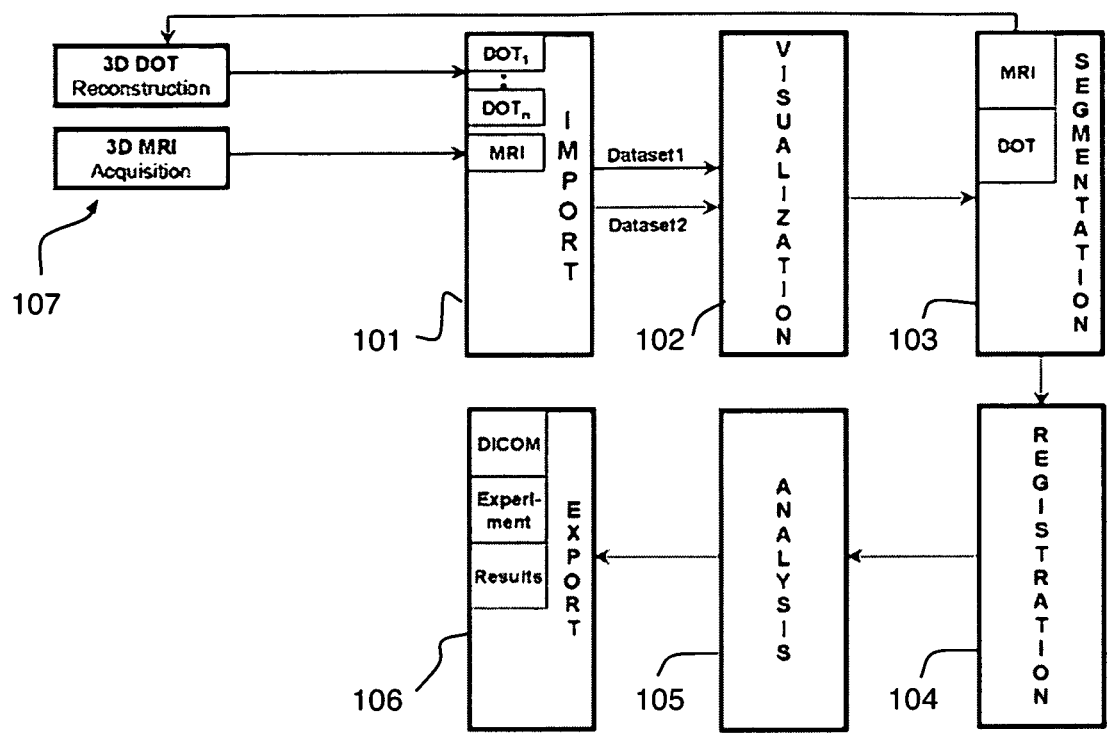
FIG. 1 is a diagram of a workflow for a platform processing multimodal optical imaging data according to an embodiment of the present disclosure.
Figure 2A:
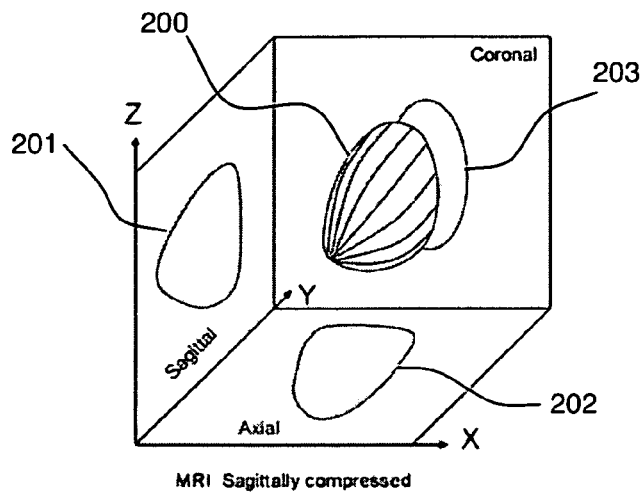
FIGS. 2A-D illustrate the generation of 2-D signatures from 3-D volumes according to an embodiment of the present disclosure.
Figure 2C:
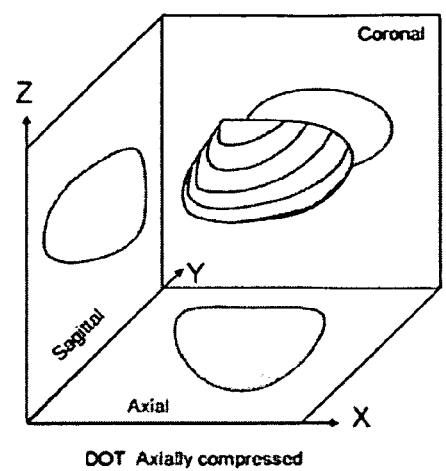
Figure 2B:
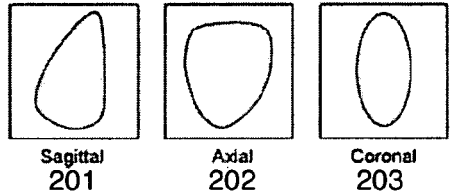
Figure 2D:
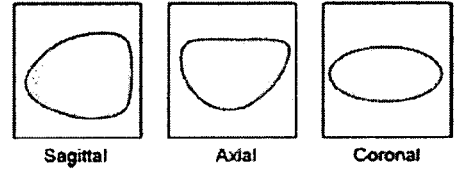

According to an embodiment of the present disclosure, a software platform combines non-concurrent MRI and DOT: the optical and multimodal imaging platform for research assessment and diagnosis. The software platform fuses and jointly analyzes multimodal optical imaging data with x-ray tomosynthesis and MR images of the breast. The software platform enables multimodal 3-D image visualization and manipulation of datasets based on a variety of 3-D rendering techniques. Through its ability to simultaneously control multiple fields of view, the software platform can streamline quantitative analyses of structural and functional data. The software platform can perform multimodal optical data visualization, fusion, and analysis, including the ability to share data and analysis results across several institutions.

Co-registration, facilitated by the software platform, combines structural and functional data from multiple modalities.

Segmentation and fusion will also enable a-priori structural information derived from MRI to be incorporated into the DOT reconstruction algorithms.

According to an embodiment of the present disclosure, a methodology for combining breast image data obtained at different times, in different geometries, and by different techniques combines data based on diffuse optical tomography DOT and magnetic resonance imaging MRI. The software platform integrates multimodal registration and segmentation algorithms. The resulting superposed 3-D tomographs facilitate tissue analyses based on structural and functional data derived from both modalities, and readily permit enhancement of DOT data reconstruction using MRI-derived a-priori structural information.

An exemplary hybrid continuous-wave (CW) and frequency-domain (FD) parallel-plane DOT system has been extensively characterized for breast cancer imaging using tissue phantoms and normal breast. The breast is softly compressed between a source plate and a viewing window in a breast box. The breast box is filled with a matching fluid, e.g., Intralipid and indian ink that has optical properties similar to human tissue. Laser diodes can be used as light sources. A grid of source positions is extracted with a given spacing. For CW transmission detection, a sample grid of pixels are extracted from the charge-coupled device CCD, which corresponds to a detector separation of the detection window. Remission detection is used to determine the average optical properties of the breast. These values are used as an initial guess for the nonlinear image reconstruction. The CCD data are used for the image reconstruction. For each source position and wavelength, FD measurements were obtained via nine detector fibers on the source plate, and CW measurements were obtained simultaneously via CCD camera in transmission. The amplitude and phase information obtained from the FD measurements are used to quantify bulk optical properties, and the CW transmission data are used to reconstruct a 3-D tomography of optical properties within the breast.

To reconstruct the absorption and scattering image, an inverse problem associated with the photon diffusion equation is solved by iterative gradient-based optimization. The algorithm reconstructs chromophore concentrations and scattering coefficients directly using data from all wavelengths simultaneously. The algorithm determines the optical properties inside a medium by adjusting these parameters, such that the difference between the modeled and experimental light measurements at the sample surface is minimized. Images of physiologically relevant variables, such as total hemoglobin concentration (THC), blood oxygenation saturation ($St(\_)$), and scattering are thus obtained.

The resulting DOT dataset is a finite element (FE) model containing nodes and tetrahedral elements. Each node is associated with the reconstructed physiological values such as THC and $St(\_)$. To facilitate registration of DOT and MR images, the FE model is automatically resampled into a 3-D voxelized volume. The smallest bounding box surrounding the FE model is identified; this volume is divided into a number of voxels, e.g., $128^3$, by default. Every voxel is associated to the tetrahedral element to which it belongs, and a physiological value is interpolated at the location of the voxel using the element's shape functions.

An example software platform enables multimodal integration and visualization of data from DOT and MRI. An exemplary workflow that a user can follow (see FIG. 1) includes input 101, visualization 102, segmentation 103, registration 104, analysis 105 and output 106:

For the input 101, the software platform accepts two types of data formats 107, e.g., MRI and DOT. Datasets are converted into a common binary format through a user interface. A patient browser in the import module 101 allows the user to select any two 3-D datasets 107 for visualization and/or registration.

For visualization 102, the visualization stage permits the user to inspect each dataset, both through volume rendering and multi-planar reformatting MPR visualization, and to define the volume of interest (VOI) through morphological operations such as punching. Punching includes determining a 3-D region of an object from the 2-D region specified on the orthographic projection of the same object. This 3-D region can then be removed or retained. This type of operation enables an editing of 3-D structures. Here, the user removes parts of the data that should not be used in the registration process.

Referring to the segmentation 103, the breast MR image segmentation technique enables a-priori structural information derived from MRI to be incorporated into the reconstruction of DOT data.

For registration, the user may decide to roughly align one volume to the other, before starting the automatic registration procedure 104.

Once the registration 104 is completed, tools are available to the user for assessment 105 of the results, including for example fused synchronized MPR, volume manipulation, and color transfer functions Referring to the 3-D DOT to 3-D MRI image registration 104; according to an embodiment of the present disclosure, the DOT and MRI images may be acquired non-concurrently. DOT images have a lower anatomical resolution and contrast than MRI, and the optical reconstruction process may a geometric model of the breast. The constraining geometric model of the breast may be semi-ellipsoid. For example, the patient breast is compressed axially in the DOT imaging device and sagitally in the MRI machine. Thus, for example, in an intensity-based image registration anatomical structures need to be aligned in the different modalities. Registration 104 includes an optimization process, which assesses image similarity and iteratively changes the transformation of one image with respect to the other, until an optimal alignment is found.

Consider two datasets to be registered to each other. One dataset is considered the reference and is commonly referred to as the "fixed" dataset. The other dataset is the one onto which the registration transformation is applied. This dataset is commonly referred to as the "moving" dataset. Registration of volumetric datasets i.e., fixed and moving involves computation of the similarity measure quantifying a metric for comparing volumes, an optimization scheme that searches through the parameter space e.g., 6-D rigid body motion to maximize the similarity measure, and a volume warping method that applies the latest computed set of parameters to the original moving volume to bring it a step closer to the fixed volume.

According to an embodiment of the present disclosure, for registration 104 2-D projection images from the two volumes for various projection geometries are determined, and a similarity measure with an optimization scheme that searches through the parameter space is created. These images are registered within a 2-D space, which is a subset of the 3-D space of the original registration transformations. These registrations are performed successively and iteratively to estimate all the registration parameters of the original problem.

Figure 8:
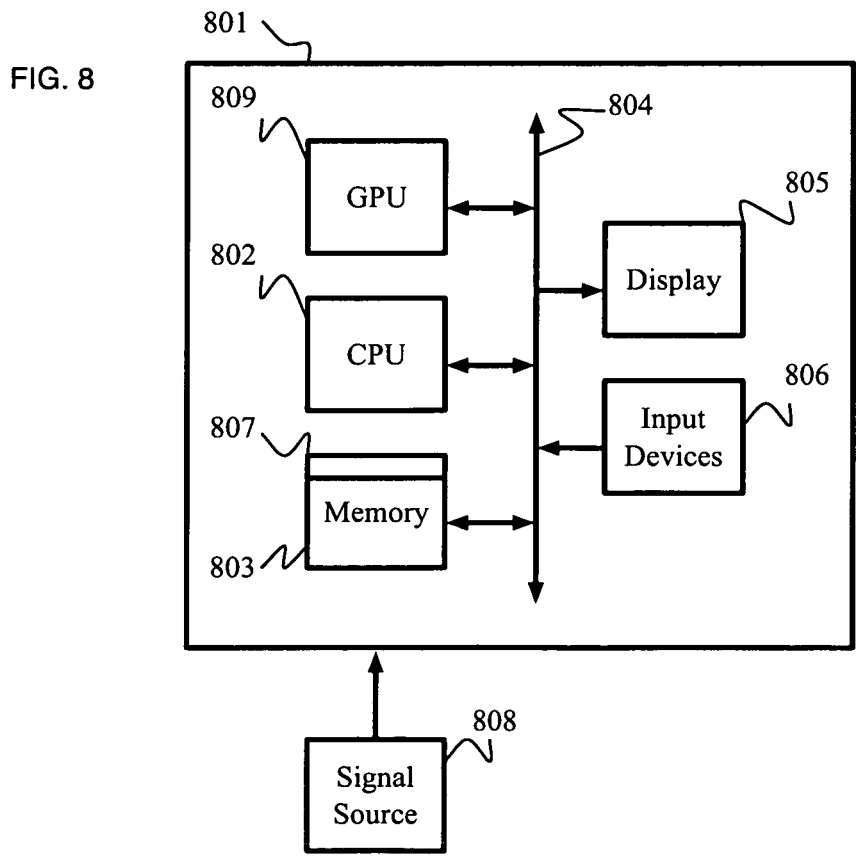
FIG. 8 is a diagram of a computer system for implementing according to an embodiment of the present disclosure.

The projection and 2-D/2-D registration similarity computation may be performed through the use of graphics processing units Graphics Processing Unit (GPU) (see 809, FIG. 8).

Multiple 2-D signatures or projections can represent the volume robustly depending on the way the signatures are generated. Referring FIGS. 2A-B and FIGS. 2C-D, to understand the idea, derive the motion of an object by looking at three perpendicular shadows, e.g., 201-203 of an object, e.g., 200.

Figure 3A:
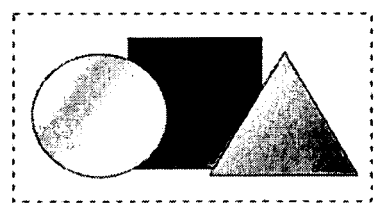
Figure 3B:
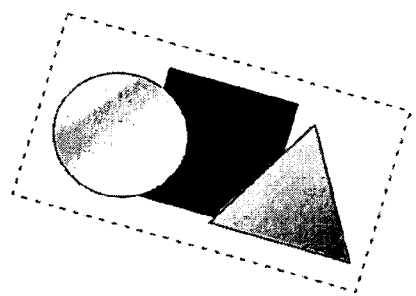
Figure 3C:
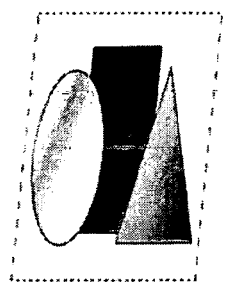
Figure 3D:
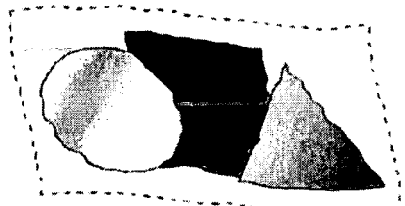

FIGS. 3B-D provide an illustration of different transformation models used in medical image registration: rigid in FIG. 3B, affine in FIG. 3C, and free-form transformations in FIG. 3D. FIG. 3A represents an original image. Non-rigid registration, depending on complexity, may be classified as an affine transformations see FIG. 3C, which include non-homogeneous scaling and/or shearing, or a free-form transformations see FIG. 3D, which include arbitrary deformations at the voxel level. These transformations can be based on intensity, shape, material properties, etc. The dominant transformation observed across the MR and DOT datasets is due to the difference in compression axis lateral compression for MR versus axial compression for DOT; this transformation can be modeled using affine parameters. DOT images do not possess enough local structure information for computation of a free-form deformation mapping to register a DOT to an MR dataset. According to an embodiment of the present disclosure, parameters including projection images, projection geometries, similarity measure, and parameter space may be used in the non-rigid registration.

Projection images: using maximum intensity projection (MIP) techniques. MIP is a computer visualization method for 3-D data that projects in the visualization plane the voxels with maximum intensity that fall in the way of parallel rays traced from the viewpoint to the plane of projection.

Projection geometries: using three mutually orthogonal 2-D MIPs to achieve greater robustness in the registration algorithm.

Similarity measure: using normalized mutual information. Mutual information measures the information that two random variables A and B share. It measures how knowledge of one variable reduces the uncertainty in the other. For example, if A and B are independent, then knowing A does not give any information about B and vice versa, so their normalized mutual information is zero. On the other hand, if A and B are identical, then all information given by A is shared with B; therefore, knowing A determines the value of B and vice versa, and the normalized mutual information is equal to its maximum possible value of 1. Mutual information quantifies the distance between the joint distribution of A and B from what it would be if A and B were independent. Here, the moving dataset is deformed until the normalized mutual information between it and the fixed dataset is maximized.

Parameter space: using rigid body motion translation and rotation, and independent linear scaling in all three dimensions. This results in a 9-D parameter space enabling non-rigid registration: three parameters for translation in x, y, and z, three parameters for rotations about three axes, and three parameters for linear scaling in each of the x, y, and z directions.

Mathematically, the estimate of the nine degrees-of-freedom DOF homogeneous transformation matrix $T^9$ is initially given by $$T^9 = \arg \max_{T^9} S^3[I_f, \Gamma^3_{T^9}(I_m)], \quad (1)$$

where $\Gamma^3_{T^9}$ is the six DOF mapping operator, $S^3$ estimates the similarity metric between two volumes, and $I_f$ and $I_m$ are the fixed and moving volumetric data, respectively. Both $\Gamma^3_{T^9}$ and $S^3$ have a superscript of 3 to indicate that the operations are more than three dimensions. The registration optimization process may be reformulated so it can be applied to each of the 2-D signatures, or projections, using the five DOF homogeneous transformation matrix defined in the plane of projection $T_p^5$. The five degrees of freedom in the plane of projection correspond to horizontal and vertical translation, horizontal and vertical scaling, and in-plane rotation. The estimate of the transformation matrix is given by:

$$T_P^5 = \arg \max_{T_P^5} S^2 \{ \Phi_P(I_f), \Gamma^2_{T_P^5}[\Phi_P(I_m)] \}, \quad (2)$$

where $\Phi_j$, is an orthographic projection operator, which projects the volume points onto an image plane, P is a 4×4 homogeneous transformation matrix, which encodes the principal axis of the orthographic projection, $\Gamma^3_{T^9}$ is a three DOF mapping operator, and $S^3$ computes the similarity metric between 2-D projections. Here, $\Gamma^3_{T^9}$ and $S^3$ have a superscript of 2 to indicate that the operations are more than two dimensions.

Since here the similarity metric is mutual information, i.e., $S^3 \blacksquare h(A)+\dot{n}(B) \ldots h(A,B)$, Eq. 2 can be rewritten as:

$$T_P^5 = \arg \max_{T_P^5}[h(A) + h(B) - h(A, B)], \quad (3)$$

where $A - \Phi_j$, $(k_i)$, $B - \Gamma^3_{T^9}[\Phi_j, (\Gamma^3_{T^9})]$, $h(x)$ is the entropy of a random variable x, and $h(x,y)$ is the joint entropy of two random variables x and y.

Entropy is a measure of variability and is defined as: $h(x)=\int p(x)$ in $p(x)dx$, and $h(x,y)=\int p(x,y)\ln p(x,y)dxdy$, where $p(x)$ is the probability density function PDF of variable x, and $p(x,y)$ is the joint PDF of variables x and y. The entropy h is discretely computed as:

$$H(I_I) = -\sum_{I=L}^{H} p_{I_I}(I) \log p_{I_I}(I) \text{ and} \quad (4)$$

$$H(I_I, I_J) = -\sum_{I=L}^{H}\sum_{J=L}^{H} p_{I_I,I_J}(I, J) \log p_{I_I,I_J}(I, J),$$

where $I_1$ and $I_L$ are two given images; and I and J are the intensities ranging from lower limit L (e.g., 0) to higher limit H (e.g., 255) for $I_k$, and $I_j$, respectively. $p_1$, (t) is the PDF of image $I_1$, and $p_{I_I,I_J}$ (I,J) is the joint PDF of images $I_I$ and $I_j$. Here, a PDF is represented by a normalized image histogram. The algorithm flowchart is shown in FIGS. 4A-B. FIG. 4A shows the global registration flowchart. For a number of iterations n 400, e.g., n=3, the three mutually orthogonal 2-D signatures are generated sagittal, coronal, and axial for both the fixed and moving volumes. After each 2-D signature generation (401A, 402A 403A), the moving 2-D signature is registered to the fixed 2-D signature (401B, 402B 403B). This process is shown schematically in FIG. 4B, and explained in detail next.

The Δ variables are initialized 410:
Δscale=Δscale_initial; Δ trans=Δ trans_initial; Δ rot=Δrot_initial.

An iterative method is initialized at block 411 and step k=1 to m may be performed as follows.

Determine the deformation steps 412:

$$\Delta\text{scale} = \frac{\Delta\text{scale}}{\text{divider}}; \Delta\text{trans} = \frac{\Delta\text{trans}}{\text{divider}}; \Delta\text{rot} = \frac{\Delta\text{rot}}{\text{divider}}.$$

Determine the initial similarity measure $S^2_{initial}$ between the two 2-D signatures 413.

Scale moving volume vertically by ± scale, then estimate $S^2_{scale\text{-}vert}$ 414. If an improvement has been made, i.e., $S^2_{scale\text{-}vert} > S^2_{initial}$, then go to next block, otherwise do not apply this scaling operation.

Scale moving volume horizontally by ± scale, then estimate $S^2_{scale\text{-}horiz}$ 415. If an improvement has been made, i.e., $S^2_{scale\text{-}horiz} > S^2_{scale\text{-}vert}$, then go to next block, otherwise do not apply this scaling operation.

Translate moving volume vertically by ± trans, then estimate $S^2_{scale\text{-}horiz}$ 416. If an improvement has been made, i.e., $S^2_{scale\text{-}horiz} > S^2_{scale\text{-}vert}$, then go to next step, otherwise do not apply this translation operation.

Translate moving volume horizontally by ± trans, then estimate $S^2_{trans\text{-}vert}$ 417. If an improvement has been made, i.e., $S^2_{trans\text{-}vert} > S^2_{scale\text{-}vert}$, then go to next block, otherwise do not apply this translation operation.

Rotate moving volume in-plane by ± rot, then estimate $S^2_{trans\text{-}horiz}$ 418. If an improvement has been made, i.e., $S^2_{trans\text{-}horiz} > S^2_{trans\text{-}vert}$, then go to next block, otherwise do not apply this rotation operation.

Convergence criteria 419: if $0 < |S^2_{rot} - S^2_{initial}| \le \Delta S^2$ or divider>divider threshold, then end k-loop 410.

If no improvements have been made, i.e., $S^2_{rot} = S^2_{initial}$, then decrease the deformation steps i.e., divider=divider×2 421.

The variables are initialized at the beginning of the registration process and may be set to, for example: n=3, m=40, Δ scale_initial=4 mm, Δ trans_initial=4 mm, Δ rot_initial=4 deg, divider_threshold=40.

According to an embodiment of the present disclosure, segmentation 103 is based on the random walker algorithm. In this case, the segmentation 103 needs little user interaction and is computationally efficient for practical applications. The segmentation 103 incorporates intensity priors, can perform multilabel, semiautomated image segmentation. Given a small number of pixels with user-defined labels, one can analytically and quickly determine the probability that a random walker starting at each unlabeled pixel will first reach one of the prelabeled pixels. By assigning each pixel to the label for which the greatest probability is calculated, high-quality image segmentation can be obtained. The segmentation 103 is formulated in discrete space i.e., on a graph using combinatorial analogs of standard operators and principles from continuous potential theory, allowing it to be applied in arbitrary dimensions.

Figure 5:
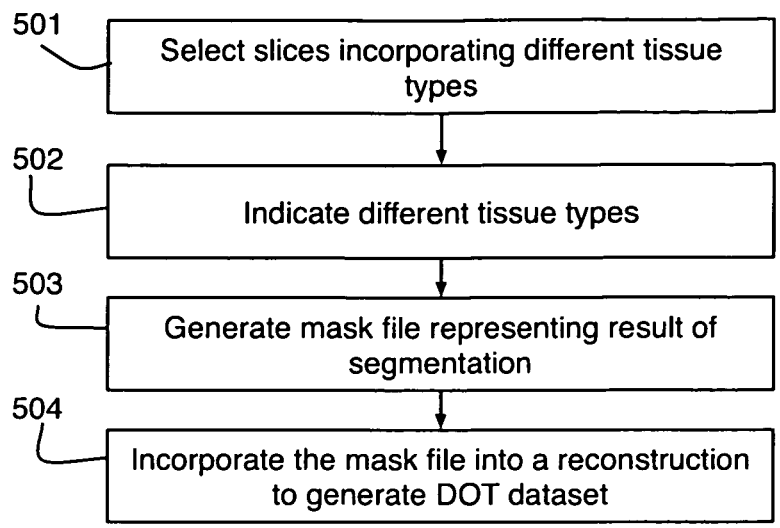
FIG. 5 is a flow chart a segmentation method according to an embodiment of the present disclosure according to an embodiment of the present disclosure.

T1-weighted MR imaging may be performed, wherein images show lipid as bright and parenchyma as dark. Tumor tissue also tends to be dark. Minimal user initialization is needed. Referring to the segmentation 103, a workflow customized for breast MRI segmentation may include:

Referring to FIG. 5, using an interactive visual interface, the user scrolls through axial, sagittal, and coronal views of the MRI dataset. In each view, the user selects one or more slices that incorporate tissue types to be segmented 501. The user draws seed points using a virtual "brush" on each of the selected slices to indicate different tissue types: e.g., fatty tissue, nonfatty tissue parenchyma and/or tumor, and outside the breast 502. A mask file is generated representing the result of the user seed point segmentation 503. Each voxel in the generated mask is assigned a value, for example, for fatty, nonfatty, or outside portions, indicating the type of tissue. The segmented mask file can be incorporated in a reconstruction of physiological quantities (such as THC) to generate the DOT dataset 504.

The segmentation can be used to distinguish fatty from nonfatty tissue and tumor from nontumor tissue. MRI segmentation may be used to isolate the tumor tissue in the image. One significant advantage of spatially registering DOT to MRI data is the ability to treat anatomical information from MRI data as prior information in the DOT chromophore concentration and scattering variables reconstruction process. By segmenting fatty from nonfatty tissue in a MR dataset for example, a-priori data can be provided about the tissue, which interacts with light in a DOT imaging device. This information can further be incorporated in solving an inverse problem associated with the photon diffusion equation, and lead to a more precise reconstruction of physiological quantities such as hemoglobin concentration. Note that in this work, the MR segmentation is not incorporated in the DOT reconstruction process.

According to an embodiment of the present disclosure, registration may be applied to various different configurations of the MRI and DOT images, for example, including incremental translations along an axis, incremental rotations about an axis, and incremental axial compression.

Figure 6:
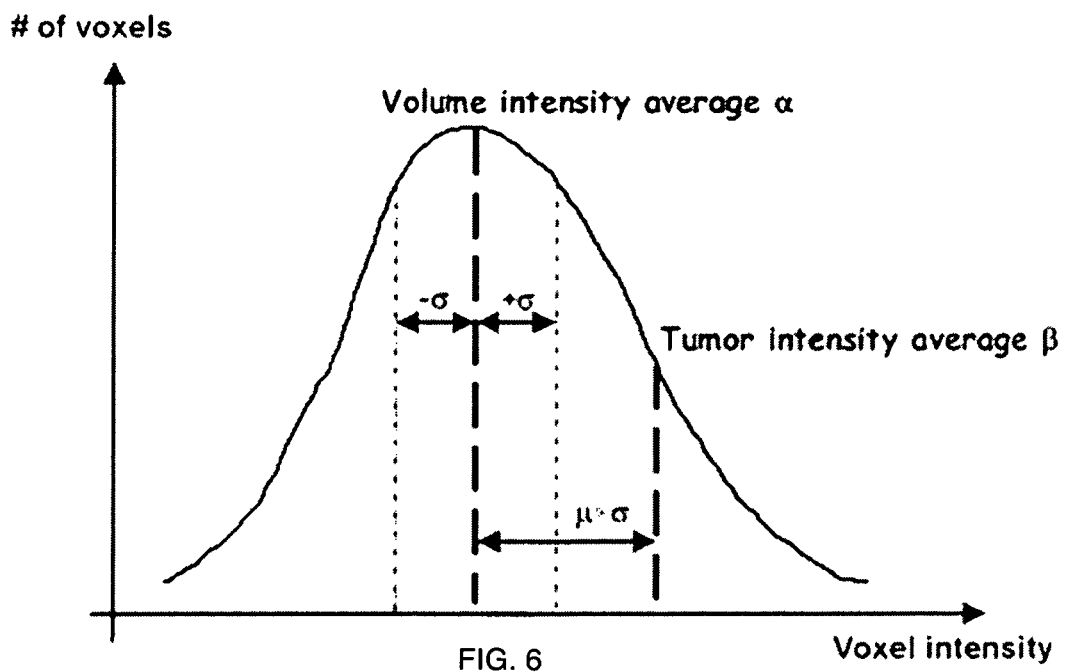
FIG. 6 is a graph if THC distribution in a DOT dataset showing resulting computed quantities after DOT-MRI image registration according to an embodiment of the present disclosure according to an embodiment of the present disclosure.

An analysis method provides functional information, for example, in the case of a carcinoma, using the MRI/DOT registered data, the differences in total hemoglobin concentration THC may be determined between the volumes inside and outside the segmented tumor by, for example, segmenting a tumor from non-tumor tissue in the breast MRI dataset, using a segmentation (see FIG. 5), determining statistical quantities from the DOT dataset, within the registered and segmented tumor and non-tumor volumes, e.g., an average THC value over the entire breast, an average THC value within the tumor volume defined by the MRI segmentation β, and/or a standard deviation of THC for the entire breast α. A new difference measure is determined, defined as the distance from α to β in terms of σ: $\mu = (\beta - \alpha)/\sigma$. The computed quantities are shown in FIG. 6 based on experimental data.

Figure 7:
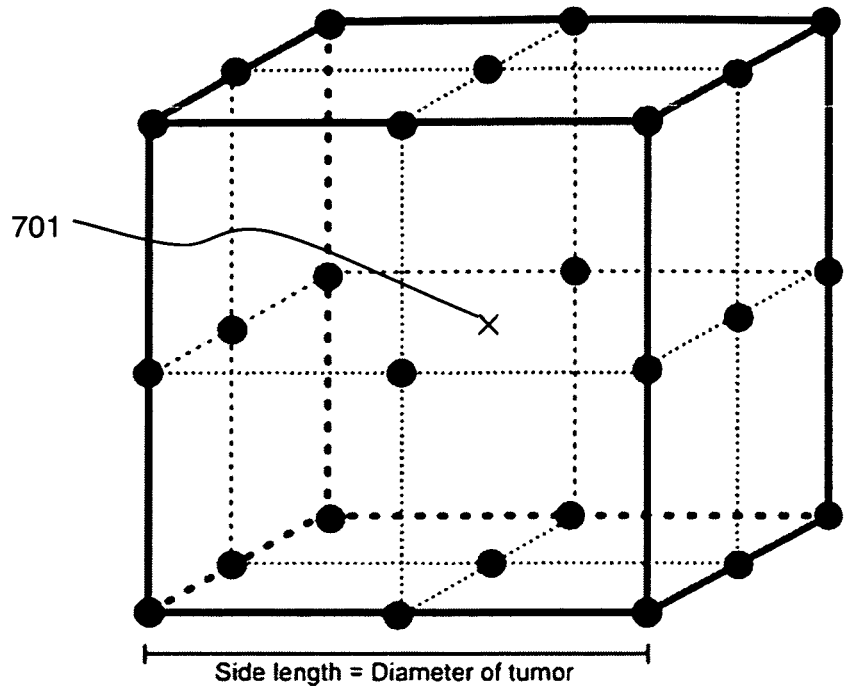
FIG. 7 is an illustration of a point arrangement on a cube and used to determine a target registration error (TRE) according to an embodiment of the present disclosure.

Referring to a phantom model validation; for registration tasks, a significant error measure is the target registration error (TRE), i.e., the distance after registration between corresponding points not used in calculating the registration transform. The term "target" is used to suggest that the points are points within, or on, the boundary of lesions. The registration gives an absolute transformation $T_{result}$, that may be applied to the DOT volume to be aligned to the MRI volume. This transformation is applied to the tumor center and neighboring points, e.g., 26 points. The points are arranged on a cube in which the tumor is inscribed. The cube shares the same center 701 as the tumor as shown in FIG. 7. The cube has a side length of 25.6 mm (substantially equal to the diameter of the tumor). The point positions resulting from the application of the absolute transformation are compared to the corresponding point positions resulting from the application of the ground truth transformation ($T_{GT}$), which gives us the expected point positions. This allows for a determination of the average TRE for each simulation. The TRE is computed as the average Euclidian distance between the 27 pairs of points ($P^i_{GT}$, $P^i_{result}$):

$$TRE = \frac{1}{27}\sum_{i=1}^{27} d(P_{GT}^i, P_{result}^i). \quad (5)$$

The volume of the tumor after registration may also be compared to the initial one, and the percentage error determined. Note that the range of translations chosen during simulations is 40 mm from −20 to 20 mm to keep a realistic aspect of the simulations. Indeed, the translations represent the patient displacements during the image acquisition, so a range of 40 mm is reasonable. Also, the range of rotations chosen is 36 deg from −18 to 18 deg for the same reasons as before. Tables 1-3 show the percent volume errors and the resulting target registration errors.

TABLE 1

Percent volume errors with respect to the original moving volume, and resulting target registration error due to incremental translations applied along the x, y, and z axes.

| Translation amount (mm) | Translation along x axis | | Translation along y axis | | Translation along z axis | |
|---|---|---|---|---|---|---|
| | Volume % error | Average TRE (mm) | Volume % error | Average TRE (mm) | Volume % error | Average TRE (mm) |
| −20 | 2.97 | 3.77 | 2.59 | 0.60 | 1.05 | 0.89 |
| −10 | 2.27 | 1.76 | 1.47 | 0.87 | −1.51 | 2.34 |
| 0 | 1.79 | 2.62 | 1.79 | 2.62 | 1.79 | 2.62 |
| 10 | 4.51 | 3.02 | 2.80 | 0.71 | 1.24 | 1.00 |
| 20 | 3.95 | 3.03 | −1.43 | 3.03 | 5.55 | 4.21 |

TABLE 2

Percent volume errors with respect to the original moving volume, and resulting target registration errors due to incremental rotations applied about the x, y, and z axes.

| Rotation amount (Degrees) | Rotation about x axis | | Rotation about y axis | | Rotation about z axis | |
|---|---|---|---|---|---|---|
| | Volume % error | Average TRE (mm) | Volume % error | Average TRE (mm) | Volume % error | Average TRE (mm) |
| −18 | 7.52 | 7.45 | 2.42 | 2.66 | 3.29 | 10.59 |
| −9 | 10.08 | 11.31 | 0.71 | 0.90 | 7.00 | 4.29 |
| 0 | 1.79 | 2.62 | 1.79 | 2.62 | 1.79 | 2.62 |
| 9 | 2.88 | 2.58 | 4.77 | 2.98 | 5.67 | 1.77 |
| 18 | 0.70 | 0.70 | −0.34 | −0.34 | 4.24 | 4.24 |

TABLE 3

Percent volume errors with respect to the original moving volume, and resulting target registration errors due to incremental axial compression of the moving volume.

| % Amount of axial compression | Volume % error | Average TRE (mm) |
|---|---|---|
| 0 | 4.91 | 1.21 |
| 10 | 3.66 | 0.87 |
| 20 | 1.80 | 1.06 |
| 30 | −0.36 | 2.37 |
| 40 | 0.11 | 2.76 |

As can be observed, the algorithm is more sensitive to rotations than translations, as the error exceeds 5% in some instances. This is explained by the fact that the algorithm uses 2-D signatures of the 3-D volume. By applying a rotation to the volume, the shape of the 2-D signature changes, whereas by applying a translation, the signature is moved compared to the volume of reference while keeping the same form. The change in form due to rotation makes the convergence of the algorithm more difficult. However, the higher level of rotations more than ±10 deg will seldom be encountered in reality, where patients usually lie prone in a reproducible manner, and will not cause such high levels of initial rotation. Tests were conducted at these higher rotations to explore the registration technique. For certain points, the error rate increases considerably. This is also explained by the use of the 2-D signatures. Indeed, when the displacement of the image exceeds the limit of the projector that captures the signature, part of the information on volume is lost, leading to a potential divergence of the algorithm. Even though the algorithm is not strictly volume preserving, because of the scaling transformation, the volume percent error shows that within the practical range of deformations, the tumor volume is preserved within an average of about 3% of its original size, which is a reasonable error. The error due to compression is always under 5%.

It is to be understood that the present invention may be implemented in various forms of hardware, software, firmware, special purpose processors, or a combination thereof. In one embodiment, the present invention may be implemented in software as an application program tangibly embodied on a program storage device. The application program may be uploaded to, and executed by, a machine comprising any suitable architecture.

Referring to FIG. 8, according to an embodiment of the present invention, a computer system 801 for coregistration and analysis of multi-modal images obtained in different geometries, inter alia, a central processing unit (CPU) 802, a memory 803 and an input/output (I/O) interface 804. The computer system 801 is generally coupled through the I/O interface 804 to a display 805 and various input devices 806 such as a mouse and keyboard. The support circuits can include circuits such as cache, power supplies, clock circuits, and a communications bus. The memory 803 can include random access memory (RAM), read only memory (ROM), disk drive, tape drive, etc., or a combination thereof. The present invention can be implemented as a routine 807 that is stored in memory 803 and executed by the CPU 802 to process the signal from the signal source 808. The computer system 801 further includes a graphics processing unit (GPU) 809 for processing graphics instructions, e.g., for processing the signal source 808 comprising image data. As such, the computer system 801 is a general purpose computer system that becomes a specific purpose computer system when executing the routine 807 of the present invention. The computer platform 801 also includes an operating system and micro instruction code. The various processes and functions described herein may either be part of the micro instruction code or part of the application program (or a combination thereof) which is executed via the operating system.

In addition, various other peripheral devices may be connected to the computer platform such as an additional data storage device and a printing device. It is to be further understood that, because some of the constituent system components and method steps depicted in the accompanying figures may be implemented in software, the actual connections between the system components (or the process steps) may differ depending upon the manner in which the present invention is programmed. Given the teachings of the present invention provided herein, one of ordinary skill in the related art will be able to contemplate these and similar implementations or configurations of the present invention.

Having described embodiments for coregistration and analysis of multi-modal images obtained in different geometries, it is noted that modifications and variations can be made by persons skilled in the art in light of the above teachings. It is therefore to be understood that changes may be made in embodiments of the present disclosure that are within the scope and spirit thereof.

What is claimed is:

1. A non-transitory computer readable medium embodying instructions executable by a processor to perform a method for coregistration of multi-modal images, the method steps comprising:
    acquiring multi-modal volumetric image data, wherein the multi-modal volumetric image data includes volumetric image data of a first modality and volumetric image data of a second modality, wherein a same tissue captured in the image data of the first and second modalities has different geometries;
    defining a volume of interest in the multi-modal volumetric image data, wherein defining the volume of interest comprises:
        determining three mutually orthogonal signatures for the first and the second modalities; and
        registering, iteratively, each of the three mutually orthogonal signatures of one of the first and the second modalities to the three mutually orthogonal signatures of the other modality, wherein registered signatures are combined into a 9-dimensional parameter space corresponding to the volume of interest;
    segmenting the volumetric image data of the first modality and incorporating priors of segmentation data of the first modality into a reconstruction of the volumetric image data of the second modality; and
    applying a registration to transform the second modality volumetric image data to align with the first modality volumetric image data according to a similarity measure through the 9-dimensional parameter space corresponding to the volume of interest, wherein an output of the registration comprises superimposed multi-modal volumetric image data wherein the geometries of the same tissue are aligned.

2. The computer readable medium of claim 1, wherein the multi-modal volumetric image data is converted into a common binary format.

3. The computer readable medium of claim 1, wherein the multi-modal volumetric image data is acquired non-concurrently.

4. The computer readable medium of claim 1, wherein the registration further comprises acquiring multiple two-dimensional projections of the volume of interest.

5. The computer readable medium of claim 4, wherein the registration is a non-rigid registration determining the similarity according to a measure of a maximum intensity projection of the two-dimensional projections.

6. The computer readable medium of claim 4, wherein the registration is a non-rigid registration determining the similarity according to a measure of a maximum intensity projection of three mutually orthogonal two-dimensional projections.

7. The computer readable medium of claim 4, wherein the registration is a non-rigid registration determining the similarity according to a measure of a normalized mutual information of the two-dimensional projections.

8. The computer readable medium of claim 4, wherein the registration is a non-rigid registration determining the similarity according to a measure of rigid body motion translation and rotation, and independent linear scaling in multiple dimensions of the two-dimensional projections.

9. The computer readable medium of claim 8, further comprising:
    generating a plurality of mutually orthogonal two-dimensional signatures for the first and second modality volumetric image data; and
    registering the second modality image data to the first modality image data after each two-dimensional signature is generated.

10. The computer readable medium of claim 1, wherein the first modality volumetric image data captures anatomical data and the second modality volumetric image data captures functional data of tissue in the volume of interest, wherein the anatomical data is prior information for the reconstruction of the volumetric image data of the second modality.

11. A method for coregistration of multi-modal images comprising:
    acquiring multi-modal volumetric image data, wherein the multi-modal volumetric image data includes volumetric image data of a first modality and volumetric image data of a second modality, wherein a same tissue captured in the image data of the first and second modalities has different geometries;
    defining a volume of interest in the multi-modal volumetric image data, wherein defining the volume of interest comprises:
        determining three mutually orthogonal signatures for the first and the second modalities; and
        registering, iteratively, each of the three mutually orthogonal signatures of one of the first and the second modalities to the three mutually orthogonal signatures of the other modality, wherein registered signatures are combined into a 9-dimensional parameter space corresponding to the volume of interest;
    segmenting the volumetric image data of the first modality and incorporating priors of segmentation data of the first modality into a reconstruction of the volumetric image data of the second modality; and
    applying a registration to transform the second modality volumetric image data to align with the first modality volumetric image data according to a similarity measure through the 9-dimensional parameter space corresponding to the volume of interest, wherein an output of the registration comprises superimposed multi-modal volumetric image data wherein the geometries of the same tissue are aligned.

12. The method of claim 11, wherein the multi-modal volumetric image data is converted into a common binary format.

13. The method of claim 11, wherein the multi-modal volumetric image data is acquired non-concurrently.

14. The method of claim 11, wherein the registration further comprises acquiring multiple two-dimensional projections of the volume of interest.

15. The method of claim 14, wherein the registration is a non-rigid registration determining the similarity according to a measure of a maximum intensity projection of the two-dimensional projections.

16. The method of claim 14, wherein the registration is a non-rigid registration determining the similarity according to a measure of a maximum intensity projection of three mutually orthogonal two-dimensional projections.

17. The method of claim 14, wherein the registration is a non-rigid registration determining the similarity according to a measure of a normalized mutual information of the two-dimensional projections.

18. The method of claim 14, wherein the registration is a non-rigid registration determining the similarity according to a measure of rigid body motion translation and rotation, and independent linear scaling in multiple dimensions of the two-dimensional projections.

19. The method of claim 18, further comprising:
generating a plurality of mutually orthogonal two-dimensional signatures for the first and second modality volumetric image data; and
registering the second modality volumetric image data to the first modality volumetric image data after each two-dimensional signature is generated.

20. The method of claim 11, wherein the first modality volumetric image data captures anatomical data and the second modality volumetric image data captures functional data of tissue in the volume of interest, wherein the anatomical data is prior information for the reconstruction of the volumetric image data of the second modality.

\* \* \* \* \*